United States Patent [19]
Raque

[11] Patent Number: 5,994,621
[45] Date of Patent: *Nov. 30, 1999

[54] FOODPLANT SEED MIXTURES

[76] Inventor: Rex R. Raque, 3872 Maidens Larne Dr., Columbus, Ohio 43221

[*] Notice: This patent is subject to a terminal disclaimer.

[21] Appl. No.: 09/046,487

[22] Filed: Mar. 23, 1998

Related U.S. Application Data

[63] Continuation-in-part of application No. 08/782,797, Jan. 13, 1997.

[51] Int. Cl.⁶ ....................................................... A01H 5/10

[52] U.S. Cl. ............................ 800/250; 800/205; 800/255

[58] Field of Search ..................................... 800/205, 250, 800/255

*Primary Examiner*—Mary E. Mosher
*Attorney, Agent, or Firm*—Thomas S. Baker, Jr.

[57] ABSTRACT

Foodplant seed for planting in a foodplant field is comprised of a mixture of a first seed for a foodplant that has been genetically modified to have a resistance to herbicide applied during emergent growth, and by a volume of a seed having an included phenotypical difference.

6 Claims, No Drawings

FOODPLANT SEED MIXTURES

This application is a Continuation-In-Part application of application Ser. No. 08/782,797, filed Jan. 13, 1997.

FIELD OF THE INVENTION

This invention relates generally to genetically-controlled foodplants, and particularly concerns seed mixtures for foodplants that are herbicide-resistant and which in-part are comprised of foodplants that have a phenotypical difference in comparison to the remaining herbicide-resistant foodplants of the seed mixtures.

BACKGROUND OF THE INVENTION

Genetically controlled foodplants such as herbicide-resistant corn plants and herbicide-resistant soybean plants are well-known and are experiencing increased usage in the United States. Unfortunately, such foodplants cannot be identified by plant characteristics from similar plants that are not resistant to a particular herbicide especially during early stages of plant growth. Persons planning to undertake field weed-control spraying using a particular herbicide are unable by inspection of the growing plants to distinguish fields of a herbicide-resistant foodplant from fields of similar foodplant that is not herbicide-resistant. The application of a weed-controlling herbicide to a field of a foodplant that is not resistant to the herbicide will result in a total field crop loss.

I have discovered that such crop losses may be minimized or eliminated through practice of the present invention. Other objectives and advantages of the present invention will become apparent from consideration of the detailed descriptions and claims which follow.

SUMMARY OF THE INVENTION

The foodplant seed mixtures of the present invention are each comprised, on a 100 parts by volume basis, of approximately from 99 parts of seed of a foodplant having resistance to a particular herbicide that is developed through genetic modification and control, and approximately from 0.001 to 1 parts of seed of that foodplant which may or may not have the same resistance to the particular herbicide but further having a foodplant phenotypical difference. Such mixture seed of the phenotypically different foodplant also may advantageously be color-coded using an externally applied stain or dye coating for enhancing pre-planting seed identification procedures.

DESCRIPTION OF THE DRAWINGS

No drawings.

DETAILED DESCRIPTION

The present invention has application to foodplants such as corn, soybeans, canola, and the like which by genetic modification or control have an included resistance to the otherwise adverse effects of a particular applied herbicide such as glyphosate herbicide or glufosinate ammonium herbicide. (Such herbicides are frequently better known by their respective trade names "Roundup" and "Liberty Link"). Although such herbicide-resistant foodplants have a herbicide resistance characteristic, they cannot during growth be distinguished from the same type of plants not having the herbicide resistance capability. Thus, at the time of planning to apply a herbicide to a particular field of the foodplant there is no manner or field inspection that will disclose whether the emerging crop is resistant to the herbicide planned for use.

To overcome this identification deficiency, I find it advantageous to plant the foodplant field with a mixture of herbicide-resistant foodplant seeds and a foodplant seed of the same or similar foodplant type. The preferred relative volume of herbicide-resistant foodplant seeds and foodplant seeds having an included phenotypical difference has been found to depend somewhat upon the particular foodplant involved. I have found that for certain larger leafed foodplants such as corn and sugar beets, fewer foodplant seeds having an included phenotypical difference are required whereas for certain smaller leafed foodplants such as soy beans and canola a greater percentage of foodplant seeds having an included phenotypical difference is preferred. Thus, larger foodplants having an included phenotypical difference are suitably visible where the field is planted with a mixture of seed comprised of, on a 100 parts by volume basis, approximately 99 to 99.999 parts herbicide-resistant foodplant seeds, and approximately 1 to 0.001 parts of foodplants having an included phenotypical difference. Smaller foodplants having an included phenotypical difference are visible where the field is planted with a mixture of seed comprised of, on a 100 parts by volume basis, approximately 90 to 97 parts herbicide-resistant foodplant seeds, and approximately 10 to 3 parts of foodplants having an included phenotypical difference. Of course, the foodplant field has greater visibility where an increased percentage volume of foodplants having an included phenotypical difference is mixed with the herbicide-resistant foodplant seed. The phenotypical difference may be a different leaf color or leaf variegation, a different leaf or plant shape, a different leaf size or plant growth height, or the like. The foodplant seeds having a phenotypical difference may or may not be herbicide-resistant. Also, the percentages stated above are approximate only and indicate preferred ranges. Of course the same objective may be obtained where the foodplant seed mixture has a greater or lesser percentage of foodplant seeds having a phenotypical difference.

With a mixture of two food plant types having phenotypically different foodplant seeds being planted in the same field, visual inspection of the emerging plants will disclose whether or not the field contains a herbicide-resistant strain of the foodplant.

Also, I find it advantageous to stain or dye the exterior coating of the phenotypically different foodplant seeds to have a different color than the exterior of the seed mixture principal seed constituent. Such provides for better pre-planting identification of the herbicide-resistant seed mixture.

Seeds for foodplants other than those particularly mentioned herein, and herbicides other than the types or examples given above, may be utilized in the practice of the present invention without departing from the meaning, scope, or intent of the following claims.

I claim my invention as follows:

1. A foodplant seed mixture comprised, on a 100 parts by volume basis, of approximately:
    99 to 99.999 parts of seed for a varietal of a foodplant genetically modified to have a resistance to a particular herbicide applied to the foodplant during emergent growth; and
    1 to 0.001 parts of seed for a varietal of said foodplant having a leaf phenotypical difference of leaf color, leaf shape, or number of leaves.

2. A foodplant seed mixture comprised, on a 100 parts by volume basis, of approximately:

90 to 97 parts of seed for a varietal of a foodplant genetically modified to have a resistance to a particular herbicide applied to the foodplant during emergent growth; and 10 to 3 parts of seed for a varietal of said foodplant having a leaf phenotypical difference of leaf color, leaf shape, or number of leaves.

3. The seed mixture of claim 1 wherein said foodplant seed for a varietal of a foodplant resistant to a particular herbicide applied to the foodplant during emergent growth is for a foodplant varietal that has a resistance to glyphosphate herbicide applied to the foodplant during emergent growth.

4. The seed mixture defined by claim 2 wherein said foodplant seed for a varietal of a foodplant resistant to a particular herbicide applied to the foodplant during emergent growth is for a foodplant varietal that has a resistance to glyphosphate herbicide applied to the foodplant during emergent growth.

5. The seed mixture defined by claim 1 wherein said foodplant seed for a varietal of a foodplant resistant to a particular herbicide applied to the foodplant during emergent growth is for a foodplant varietal that has a resistance to glufosinate ammonium herbicide applied to the foodplant during emergent growth.

6. The seed mixture defined by claim 2 wherein said foodplant seed for a varietal of a foodplant resistant to a particular herbicide applied to the foodplant during emergent growth is for a foodplant varietal that has a resistance to glufosinate ammonium herbicide applied to the foodplant during emergent growth.

* * * * *